United States Patent
Bourne

(10) Patent No.: US 9,155,812 B1
(45) Date of Patent: Oct. 13, 2015

(54) VENT STICK AIR FRESHENER WITH DUAL ACTION BODIES AND AIR FLOW TUNNEL

(71) Applicant: American Covers, Inc., Draper, UT (US)

(72) Inventor: Christopher Bourne, Draper, UT (US)

(73) Assignee: American Covers, Inc., Draper, UT (US)

( * ) Notice: Subject to any disclaimer, the term of this patent is extended or adjusted under 35 U.S.C. 154(b) by 29 days.

(21) Appl. No.: 14/281,345

(22) Filed: May 19, 2014

(51) Int. Cl.
*A61L 9/12* (2006.01)

(52) U.S. Cl.
CPC .................................... *A61L 9/12* (2013.01)

(58) Field of Classification Search
CPC ............... A61L 9/00; A61L 9/02; A61L 9/03; A61L 9/04; A61L 9/12
USPC ............ 422/120, 123; 239/34, 44, 53, 55, 56, 239/60
See application file for complete search history.

(56) References Cited

U.S. PATENT DOCUMENTS

| | | | |
|---|---|---|---|
| 1,683,545 A | 9/1928 | Harris | |
| 3,847,305 A | 11/1974 | Tobin | |
| D250,041 S | 10/1978 | Schimanski | |
| 4,149,675 A | 4/1979 | Van Breen et al. | |
| 4,226,944 A | 10/1980 | Stone et al. | |
| RE32,834 E | 1/1989 | Cordits et al. | |
| 4,808,347 A | 2/1989 | Dawn | |
| 5,368,822 A | 11/1994 | McNeil | |
| 5,422,078 A | 6/1995 | Colon | |
| 5,651,522 A | 7/1997 | Davis et al. | |
| 5,704,832 A | 1/1998 | Borrell | |
| 5,762,549 A | 6/1998 | Scheuer et al. | |
| D397,603 S | 9/1998 | Eggert et al. | |
| 5,861,128 A | 1/1999 | Vick et al. | |
| 5,899,382 A | 5/1999 | Hayes et al. | |
| D411,002 S | 6/1999 | Farmer | |
| D415,268 S | 10/1999 | Farmer | |
| D417,727 S | 12/1999 | Christianson | |
| 6,123,906 A | 9/2000 | Farmer | |
| D437,038 S | 1/2001 | Chuan | |
| D437,041 S | 1/2001 | Eisenbraun | |
| 6,190,607 B1 | 2/2001 | Farmer | |
| 6,197,263 B1 | 3/2001 | Blount | |
| 6,264,887 B1 | 7/2001 | Farmer | |
| 6,416,043 B1 | 7/2002 | Eisenbraun | |
| D507,341 S | 7/2005 | Taylor | |

(Continued)

OTHER PUBLICATIONS http://shop.advanceautoparts.com/webapp/wcs/stores/servlet/product_6170795-P_N3004 . . . Advance Auto Part; Arometrics Dual-Scent Vent-Juicy Strawberry and Vanilla; 1 Page; accessed Dec. 10, 2010.

(Continued)

*Primary Examiner* — Sean E Conley

(74) *Attorney, Agent, or Firm* — Thorpe North & Western LLP

(57) ABSTRACT

A vent stick air freshener has a pair of vent rods extending rearwardly from an annular head with a hollow therein, an open front end and an open rear end defining an air tunnel. At least one body is carried by at least one of the pair of vent rods. An insert is at least partially received in the hollow of the annular head. A space is defined between the insert and the annular head. The at least one body or the insert or both has a desired scent material interspersed therein and diffusible out over time.

24 Claims, 3 Drawing Sheets

(56) References Cited

U.S. PATENT DOCUMENTS

| | | |
|---|---|---|
| 7,137,570 B2 | 11/2006 | Wheatley |
| 7,159,792 B2 | 1/2007 | Wheatley et al. |
| 7,293,719 B2 | 11/2007 | Wheatley |
| D594,953 S | 6/2009 | King et al. |
| D594,954 S | 6/2009 | Wheatley |
| D604,825 S | 11/2009 | Brandenburg |
| 7,687,037 B2 | 3/2010 | Wheatley et al. |
| 7,687,038 B2 | 3/2010 | Wheatley et al. |
| D619,692 S | 7/2010 | Hami et al. |
| D619,693 S | 7/2010 | Hami et al. |
| D619,694 S | 7/2010 | Hami et al. |
| D620,573 S | 7/2010 | Hami et al. |
| D625,798 S | 10/2010 | Hami et al. |
| D640,359 S | 6/2011 | Irvin |
| D640,781 S | 6/2011 | Brandenburg |
| D650,892 S | 12/2011 | Wheatley et al. |
| 8,147,761 B2 | 4/2012 | Wheatley et al. |
| D667,100 S | 9/2012 | Hakim |
| D684,675 S | 6/2013 | Irvin et al. |
| 8,460,609 B1 | 6/2013 | Wheatley et al. |
| 8,480,960 B2 | 7/2013 | Wheatley et al. |
| D699,334 S | 2/2014 | Alesi et al. |
| 8,685,330 B2 | 4/2014 | Irvin et al. |
| D712,022 S | 8/2014 | Hakim |
| 2003/0202922 A1 | 10/2003 | Farmer |
| 2005/0169793 A1 | 8/2005 | Wheatley et al. |
| 2006/0279008 A1 | 12/2006 | Jursich |
| 2010/0065654 A1 | 3/2010 | Wheatley et al. |
| 2011/0108632 A1 | 5/2011 | Brandenburg et al. |
| 2014/0113538 A1* | 4/2014 | Irvin et al. .................. 454/156 |

OTHER PUBLICATIONS http://www.bestliquidations.com/Medo_Vent_Frehser.htm: BestLiqudations.com; Medo Vent Fresh Air Fresheners; 2 pages; accessed Dec. 10, 2010.

Medo® Air Fresheners; Auto Expressions™ 2005 Product Catalog; 25 pages.

Pictures (3) of Medo® auto Expressions Vent™ Air Freshener distributed by SOPUS Products of Moorpark, CA 2003 copyright date on package.

www.chicscents.com/Products.aspx Island Adventure Sandals; 2 pages; accessed Feb. 1, 2011.

www.chicscents.com/Products.aspx; Inspiration 3-D by Chic; 2 pages; accessed Feb. 1, 2011.

www.autothing.com/Products/Air%Fresheners/air%20freshener-clip.htm ; Air Fresheners Fresh Scents for your mobile life, Clip-on Air Vent Clips from Eagle O, Accessed Aug. 12, 2008, 1 page.

U.S. Appl. No. 29/494,602, filed Jun. 23, 2014; Chris Bourne.

* cited by examiner

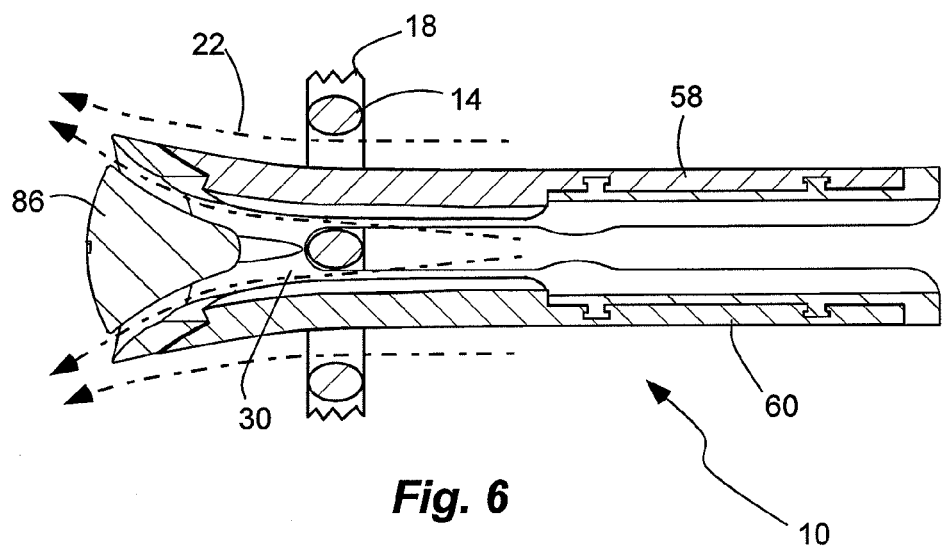
Fig. 6
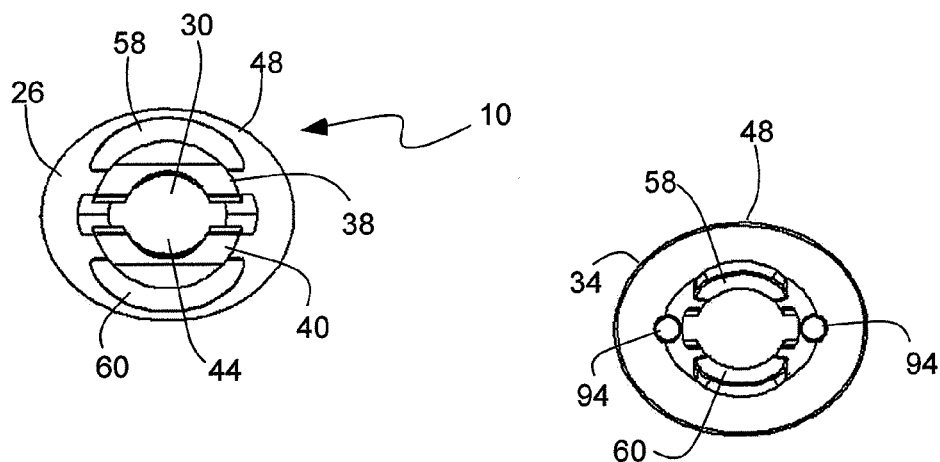
Fig. 7
Fig. 8

VENT STICK AIR FRESHENER WITH DUAL ACTION BODIES AND AIR FLOW TUNNEL

BACKGROUND

1. Field of the Invention

The present invention relates generally to air fresheners. More particularly, the present invention relates to a vent stick air freshener.

2. Related Art

Various types of vent stick air fresheners have been proposed. For example, see U.S. Pat. Nos. 7,687,038; 7,687,037; 8,147,761; 8,480,960; 8,460,609; 8,685,330; D594,954; D640,359; D650,892; D684,675. The development and improvement of air fresheners, and vent stick air fresheners, is an ongoing endeavor.

SUMMARY OF THE INVENTION

It has been recognized that it would be advantageous to develop an improved air freshener, such as a vent stick air freshener, that can provide a desired scent, and/or odor eliminating capabilities. In addition, it has been recognized that it would be advantageous to develop an air freshener that can efficiently disperse the desired scent and/or odor eliminating material.

The invention provides a vent stick air freshener for use with a louver of an air vent. The air freshener has an annular head to extend from the louver, and has a hollow therein, an open front end and an open rear end defining an air tunnel through the annular head. A pair of vent rods extends rearwardly from the annular head, and extends through the louver into the air vent. A gap between the pair of vent rods receives the louver. At least one body is carried by at least one of the pair of vent rods. An insert is at least partially received in the hollow of the annular head. A space is defined between the insert and the annular head. The at least one body or the insert or both has a desired scent material interspersed therein and diffusible out over time.

In accordance with a more detailed aspect of the invention, another one of the at least one body or the insert can have an odor eliminating material, different from the scent material, interspersed therein.

In addition, the invention provides a vent stick air freshener for use with a louver of an air vent. The air freshener has a body with a head extending from the louver, and an pair of vent rods extending rearwardly from the head and through the louver into the air vent. A gap between the pair of vent rods receives the louver. A pair of elongated notches is each one formed in a different one of the pair of vent rods. A pair of scented bodies has a desired scent material interspersed therein and diffusible out over time. Each one of the scented bodies is disposed in a different one of the pair of notches in the pair of vent rods. A cavity is formed in the head of the body. An air tunnel is disposed in the body and extends from the cavity in the head to the gap between the pair of vent rods. An insert is at least partially received in the cavity of the head. An annular gap is defined between the insert and the head, and is in fluid communication with the tunnel.

In accordance with a more detailed aspect of the invention, the insert can have an odor eliminating material interspersed therein, different than the scent material of the pair of scented bodies.

Furthermore, the invention provides a vent stick air freshener for use with a louver of an air vent. The air freshener has an elongated tubular body with a hollow therein and an open front end. A rear of the body is bifurcated to form a pair of vent rods configured to extend through the louver into the air vent. A gap is defined between the pair of vent rods to receive the louver. An annular head is defined in the body forward of the pair of vent rods, and extends from the louver. At least one body is carried by at least one of the pair of vent rods. An insert is at least partially received in the hollow of the annular head. A space is defined between the insert and the annular head. The at least one body or the insert or both has a desired scent material interspersed therein and diffusible out over time.

In accordance with a more detailed aspect of the invention, another one of the at least one body or the insert can have an odor eliminating material, different from the scent material, interspersed therein.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 6 is a cross-sectional side schematic view of the vent stick air freshener of FIG. 1;

FIG. 7 is a rear view of the vent stick air freshener of FIG. 1; and

FIG. 8 is a front view of the vent stick air freshener of FIG. 1, shown with an insert removed.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

The present invention provides an air freshener, and namely a vent stick air freshener, that can be utilized with an air vent having one or more louvers extending across the air vent, and through which air blows. Such an air vent can be found in a vehicle. The vent stick air freshener can provide a desired scent material, interspersed within a body thereof, and diffusible out of the body over time. In another aspect, the vent stick air freshener can provide an odor eliminating material that can also be interspersed within a body or insert thereof. In another aspect, the vent stick air freshener can provide both a desired scent material, interspersed within a body thereof, and diffusible out of the body over time, and an odor eliminating material that can also be interspersed within another body or insert thereof. Thus, one body can provide a desired scent, while the other body can eliminate odor, or carry a material that can eliminate odor. In addition, the vent stick air freshener can provide an air tunnel through which air can flow, and which can expose opposite or multiple sides of one of the bodies to the flow of air. Furthermore, the vent stick air freshener can be shaped to help diffuse the air flow, and thus the desired scent, and/or odor eliminating material.

Figure 1:
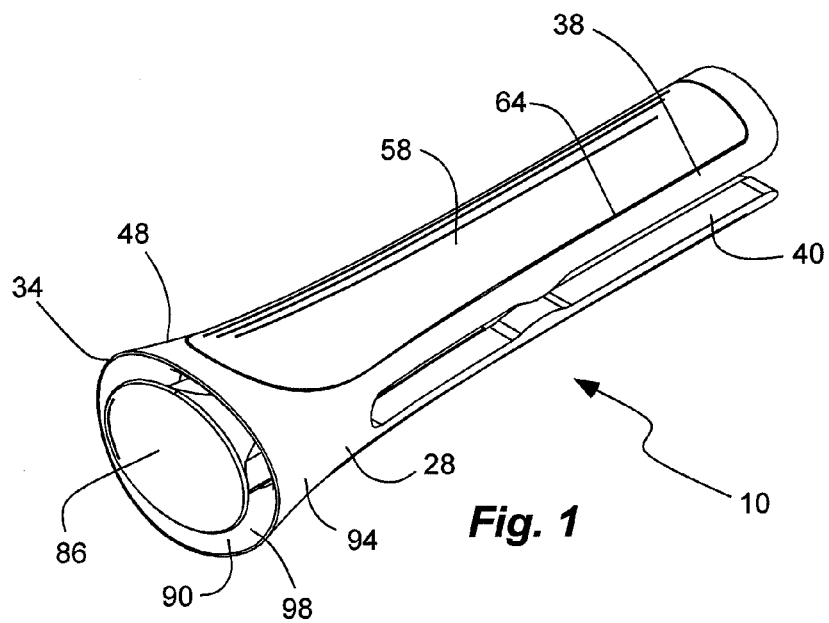
FIG. 1 is a perspective view of a vent stick air freshener in accordance with an embodiment of the present invention.
Figure 2:
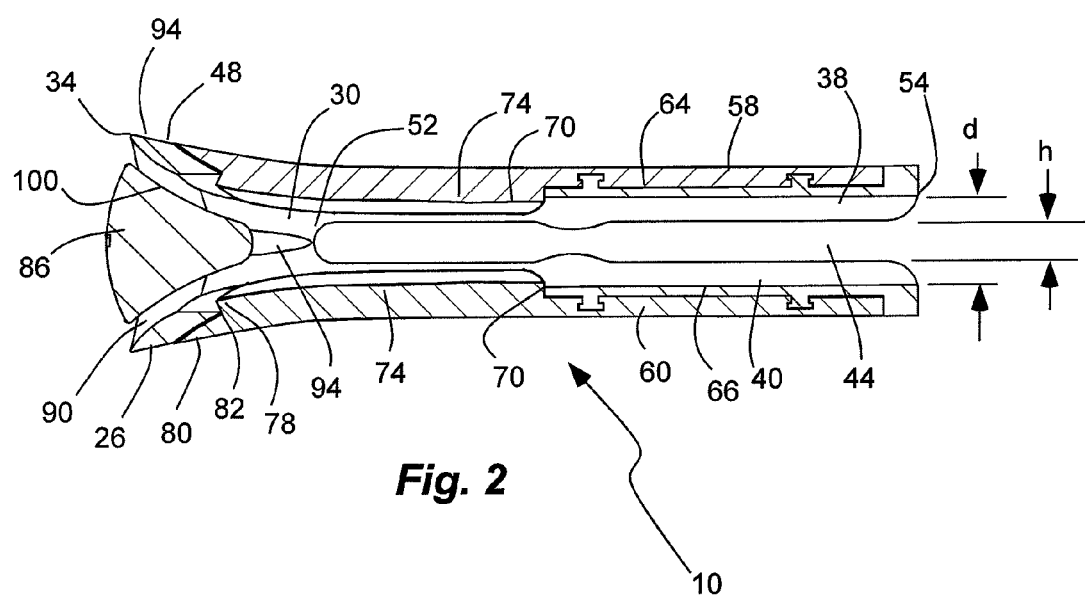
FIG. 2 is a cross-sectional side view of the vent stick air freshener of FIG. 1 taken along line 2-2 in FIG. 3.
Figure 3:
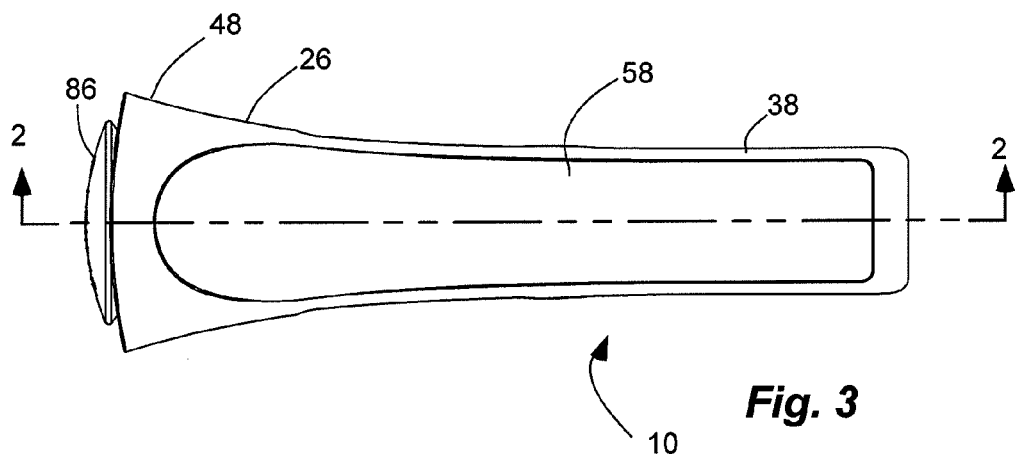
FIG. 3 is a top view of the vent stick air freshener of FIG. 1.
Figure 4:
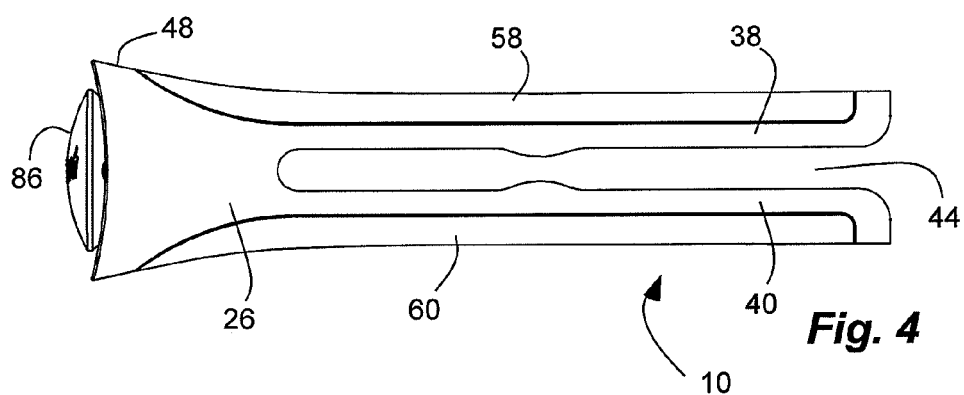
FIG. 4 is a side view of the vent stick air freshener of FIG. 1.
Figure 5:
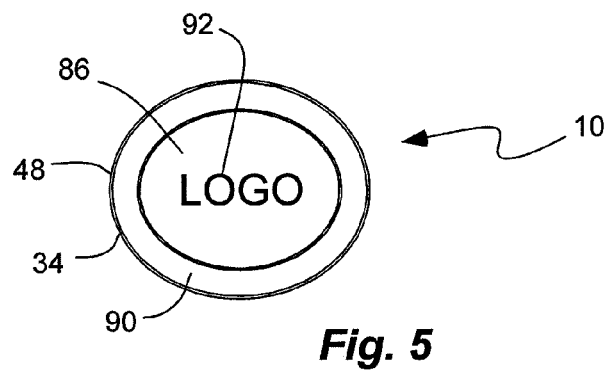
FIG. 5 is a front view of the vent stick air freshener of FIG. 1.

As illustrated in FIGS. 1-8, a vent stick air freshener, indicated generally at 10, in an example implementation in accordance with the invention is shown carried by a louver 14 of an air vent 18 (FIG. 6). Air can be forced through the air vent, indicated by dashed arrows 22. Thus, the air freshener can be disposed in the air flow from the air vent.

The air freshener 10 can include an elongated body 26, that can be tubular or can be an elongated tubular body, having a hollow 30 therein, and an open front end 34. A rear of the body 26 can be bifurcated to form a pair of vent rods 38 and 40 that can extend through the louver 14 into the air vent 18 (FIG. 6). A gap 44 is defined between the pair of vent rods 38 and 40 to receive the louver 14 (FIG. 6). The gap can extend a majority of the length of the body such that a majority of the length of the body is the pair of vent rods. An annular head 48 is defined in the body 26 forward of the pair of vent rods 38 and 40, and extends from the louver 14 or in front of the louver 14 (FIG. 6). The annular head 48 can be hollow or have a cavity therein, and the hollow 30 can extend through the head 48, from the open front end 34 to an open rear end (52 or 54) of the head or the body, and to the gap 44, defining an air tunnel through the body and the head. Thus, the air tunnel can be disposed in the body, and can extend from the cavity in the head, to the gap between the pair of vent rods. The gap 44 and the hollow 30 can be substantially collinear. Thus, the air tunnel can extend continuously through the gap, between the pair of vent rods, around the louver, and through the head. The pair of vent rods 38 and 40 can extend rearward from the annular head 48, such as from opposite sides of the annular head. The gap between the pair of vent rods has a gap height h between the pair of vent rods, that is narrower or less than a diameter d of the air tunnel. Thus, the vent rods can accommodate an aperture, as discussed below. In addition, the pair of vent rods can have a cross-sectional shape that is arcuate, as shown in FIG. 7.

The air freshener has at least one body 58 carried by at least one of the pair of vent rods 38. The air freshener can have a pair of bodies 58 and 60 carried by the pair of vent rods 38 and 40, respectively; or each one carried by a different one of the pair of the pair of vent rods. In one aspect, the bodies 58 and 60 can be scented bodies with a desired scent material interspersed therein and diffusible out over time to prove a desired scent. In another aspect, the bodies 58 and 60 can be neutralizing bodies with a neutralizing agent interspersed therein and diffusible out over time to neutralize odors.

The pair of vent rods 38 and 40 can have a pair of elongated notches 64 and 66, respectively; or each one formed in a different one of the pair of vent rods. Each one of the bodies 58 and 60 can be disposed in the pair of notches 64 and 66, respectively; or each can be disposed in a different one of the pair of notches in the pair of vent rods. The bodies 58 and 60 can be flush with a surface of the vent rods 38 and 40 contiguous with and surrounding the bodies. Thus, the air flow 22 can flow smoothly across the bodies and the vent rod or body 26. The notches can extend from the head substantially the entire length of the body 26, but with a portion of the head and a distal end of the vent rods bounding the opposite distal ends of the notches, and thus the bodies. Thus, the bodies can also extend substantially the entire length of the body to maximize surface area to diffuse scent or neutralizing agent. The bodies 58 and 60 can have a size and shape similar to the size and shape of the vent rods 38 and 40. Thus, the bodies can have a length longer than a width. The bodies can have an exposed or exterior side or surface, with indicia thereon.

In addition, each of the elongated notches 64 and 66 can have an aperture 70 in the notch and extending into the air tunnel or hollow 30. The apertures can be located at forward end of the notch, adjacent the head 48. Each of the bodies 58 and 60 can have a portion 74 extending therefrom and into the aperture 70. Thus, the portions 74 of the bodies 58 and 60 can be exposed to the air tunnel or hollow 30, and the flow of air therethrough, to further disperse the scent or neutralizing agent. The portion 74 can extend along a significant portion of the length of the bodies, such as approximately half of the length of the bodies.

The bodies 58 and 60 can be attached to the body 26 or the vent rods 38 and 40 in any appropriate manner. In one aspect, the bodies 58 and 60 can be snap fit in the elongated notches 64 and 66. The vent rods 38 and 40, or the notches 64 and 66, can include protrusions with enlarged heads to be inserted into cavities with narrower necks or openings therein formed in the bodies 58 and 60. In addition, the bodies 58 and 60 can each have a front lip 78, or pair of lips 78 and 80 separated by a notch 82. A lower lip 78 can extend into the aperture 70 in the notch 64 or 66, and can extend under the head 48. An upper lip 80 can extend over the head 48. A portion of the head 48 adjacent the aperture 70 can be received in the notch 82 between the lips. Thus, a forward portion of the bodies can extend across the aperture and be secured to the head.

In addition, the air freshener 10 can have an insert 86 carried by the head 48, and at least partially received in the hollow 30 or cavity of the annular head. The insert 86 can be positioned in the head or hollow so that a space 90 is defined between the insert and the head, or interior thereof. The space 90 can be annular, and can circumscribe or surround the insert 86. The space is in fluid communication with the tunnel. Thus, the air flow can flow through the gap between the vent rods, and through the hollow or cavity in the head and around the insert. The insert 86 can be formed of a compressible and/or elastic material, and can be press fit between a pair of posts 94 (FIG. 8 showing head with the insert removed) in the head. Thus, the insert can have an interference fit with the pair of posts, and can be removable. In another aspect, the insert can be snap fit into the hollow, or onto a post. In another aspect, the insert can be adhered on a post.

The insert 86 can have a broad forward facing surface with a convex curvature. Indicia 92 (FIG. 5) can be disposed on the surface. The indicia can be a logo, or other information.

The annular head 48 can flare outwardly to help disperse the air flow from the air vent. The head 48 can have an exterior surface with a portion 94 laterally circumscribing the head and with a concave conical shape to direct air flow from around an exterior of the air freshener or body in an outward direction. In addition, the head 48 can have an interior surface 98 circumscribing and surrounding the insert 86 and with a convex conical shape.

The insert 86 can have an exterior surface 100 with a concave conical shape spaced-apart from the convex conical shape of the interior surface 98 of the head. Thus, the space 90 can have an annular shape that is conical and curved to disperse the air flow from within the air tunnel.

In one aspect, the insert 86 can have

In another aspect, the insert 86 can have an odor eliminating material. The odor eliminating material can be interspersed therein, and diffusible out over time. In another aspect, the odor eliminating material can absorb undesired scents.

As described above, the body(ies) 58 and 60 and the insert 86 can have the desired scent material interspersed therein and diffusible out over time. In one aspect, the body(ies) and the insert can have different, and/or complimentary, scents or scent material. The body(ies) can have a greater volume and/or surface area (or exposed surface area) than a volume and/or surface area of the insert. Thus, the scent or scent material in the body(ies) can be predominant, while the scent or scent material in the insert can be less predominant or strong.

In another aspect, the body(ies) 58 and 60 and the insert 86 can have the desired scent material, and the insert 86 can have the odor eliminating material. Thus, a greater number and/or size or volume of the desired scent can be provided, and can be positioned along the exterior of the body 26, to provide a greater dispersal of the desired scent (with respect to the odor elimination); while an odor eliminating (or absorbing) material can be positioned closer to a likely location of the undesired scent, i.e. in front of the air vent. In another aspect, the body(ies) 58 and 60 can have the odor eliminating material, and the insert 86 can have the desired scent material. Thus, a greater number and/or size or volume of the odor eliminating material can be provides, and can be positioned along the exterior of the body 26, to provide a greater dispersal of the odor eliminating material (with respect to the desired scent); while a desired scent material can be positioned closer to a likely location of a user, i.e. in front of the air vent. Thus, at least one of the at least one body or the insert has a desired scent material interspersed therein and diffusible out over time, and another one of the at least one body or the insert has an odor eliminating material, different from the scent material, interspersed therein.

As described above, the scent material can be carried by the body(ies) 58 and 60, which in turn can be carried by the vent rods 38 and 40. In addition, the scent material can be carried by the insert 86, which in turn can be carried by the head 48. The scent material can be in a polymer body. Thus, the body(ies) 58 and 60, and/or the insert 86, can be formed of polymer, and can be polymer bodies, and can define a carrier material.

The polymer body can be flexible and resilient, such as a polymer gel. The polymer body can be elastic and coherent. Thus, the polymer body can be compressible under an applied force, and substantially returnable to an original configuration upon removal of the applied force. It has been found that the polymer gel provides desired characteristics of aesthetics, flexibility, longevity, substantially constant scent release, and containment. In accordance with another aspect of the present invention, the polymer gel can have a freestanding, self-supported, three-dimensional shape that does not significantly change as the scent is released. The carrier material or polymer body can have a scent material of the desired scent or neutralizing agent interspersed therein. The scent material or neutralizing agent can disperse or diffuse out of the carrier material or polymer body into the air or atmosphere where it can be detected, or where it can provide a discernable scent, or can neutralize odors. It is believed that the scent material migrates or diffuses through and out of the carrier material or polymer body. The scent material can be high in volatile notes, or has high volatility and can vaporize or evaporate at low temperatures. The scent material can include a scented oil. For example, suitable scent material can include pine, berry, vanilla, apple, coconut, cherry, pina colada, etc.

The carrier material or polymer body can include a polymer material, such as a polymer gel. The polymer body and/or polymer gel can be elastic and coherent. Thus, the polymer body can elastically deform under normal conditions. The polymer body can be flexible and resilient, such that the body or gel can compress under an applied force, but can substantially return to its original configuration upon removal of the applied force. The polymer gel, or the polymer body, can have a freestanding, self-supported, three-dimensional shape. Thus, the polymer gel or polymer body can be consistent or solid enough to support or maintain its shape in a freestanding manner without a container. The three-dimensional shape can be any desired shape. The polymer gel can be considered a solid material that is elastic and coherent, and thus flexible and capable of being deformed, but without being flowable. Thus, the polymer gel may have a sufficiently high molecular weight, and/or a sufficiently high viscosity, so that it is a non-flowable gel. In addition, the polymer gel can be considered as stable. Thus, the polymer gel can be bendable, but otherwise substantially maintains its form. The polymer body or polymer gel can be characterized as a polymeric material in the glass state with substantially no macroscopic flow. The polymeric material can have a glass transition temperature greater than approximately 110° F. The polymer gel can retain its gel-like characteristic over time, without drying or cracking, and without becoming hard or brittle.

In one aspect, the polymer gel or polymer body can include a polyurethane material or can be a polyurethane gel. The gel can be formed by combining a polyurethane material with a scented oil. Surprisingly, it has been found that such a combination provides a desired scent, but without staining or substantially leaking onto a surface. In addition, the polymer body does not undergo a visually ascertainable physical change, such as drying out or cracking. Thus, the polymer body remains aesthetically pleasing.

In some aspects, a scented oil and a polymerizable monomer can be combined, along with optional initators or other reactants. Isocyanate reaction polymers have shown good results in connection with the present invention. For example, the polymer gel and scent material can be a urethane polymerization product of combining a scented oil with a polyether polyol, and then with a diphenylmethane diisocyanate (MDI) prepolymer. Therefore, in some embodiments, the scent material can be a scented oil which participates in the polymerization reaction between polymerization reactants. For example, essential oils such as terpenes and the like can be mixed with polymerization reactants, or even in place of some reactants. Without being bound by any particular theory, it is thought that at least some of the reduction or elimination in residue in the devices of the present invention result from at least partial replacement of mineral oils and/or polyols with scented oils such as those listed herein. Other suitable isocyanates can include, but are not limited to, tolylene diisocyanates, methylene diphenyl isocyanates, hexamethylene diisocyanates, prepolymers thereof, and the like. Those skilled in the art will recognize various other isocyanate reaction polymers, i.e. polyurethanes, which can be suitable for use in connection with the present invention.

Alternatively, the polymer gel or polymer body can include silicone, diffused polyurethane, polyvinylchloride (PVC), ethylene vinyl acetate (EVA), thermoplastic polyurethane (TPU), a polymer encapsulation fragrance delivery platform (PolyIFF®), thermoplastic elastomer (TPE), polypropylene, ethylene/methacrylic acid (E/MAA) copolymer, in which the MAA groups have been partially neutralized with lithium ions (Surlyn Dupont), etc.

As a general guideline, the polymer gel or polymer body can be formed of an elastomer such as, but not limited to, urethanes (including polyester and polyether polyol/isocyanate polymerization products), polyacrylates, polybutadienes, ethylene propylene elastomers, silicones, natural and synthetic rubbers, styrene/butadiene block copolymers, and the like. In some embodiments, the polymer gel can be formed of a thermoplastic elastomer. Thermoplastic elastomers can be block copolymers such as polyurethanes, polyamides, copolyesters, and styrene-butadiene-styrene polymers. Other thermoplastic elastomers can be elastomer/thermoplastic blends such as ethylene-propylene-diene monomer in an isotactic polypropylene phase or nitrile rubber dispersed in a PVC phase. As used herein, "thermoplastic elastomer" refers to an elastomer which can be heated and processed like thermoplastic materials. Specifically, a thermoplastic elastomer can be heated to a melted or flowable state and then cooled, resulting in reformation of cross-linking and subsequent coherency without a substantial change in mechanical properties such as strength, flexural modulus, elastic modulus, etc.

As used herein, "elastomeric polymer" and "elastomer" may be used interchangeably and refer to a polymeric material which can be mechanically deformed and upon release returns to an original shape. A coherent elastomer is also non-flowable at or near room temperatures. Further, "cling" and "clingy" refer to a property of a polymeric material which imparts adhesion to most surfaces without a loss of coherency in the polymer. Typically, removal of an elastomeric polymer body with a clingy attachment surface from a substrate does not result in substantial deformation, including temporary deformation, during flexing of the elastomer and/or attachment surface. A clingy attachment surface can be provided directly by the polymer body or can be provided in a separate layer as discussed in more detail herein. Adhesion can occur via mechanical adhesion or specific adhesion. Specific adhesion refers to adhesion dominated, or entirely characterized, by secondary intermolecular forces, i.e. non-covalent bonds, although some covalent bonds can be formed. Although the polymer gel or polymer body is freestanding and self-supporting, it is also flexible and resilient. Thus, polymer body or carrier material can form a flexible and resilient structure or body that can be selectively deformed and can return substantially to the three-dimensional shape. In addition, the carrier material or polymer body can be opaque. Alternatively, the carrier material or polymer body can be light transmissive in at least a translucent manner.

Various aspects of vent stick air fresheners are disclosed in U.S. Pat. Nos. 7,687,038; 7,687,037; 8,147,761; 8,480,960; 8,460,609; 8,685,330; D594,954; D640,359; D650,892; and D684,675; and U.S. patent application Ser. Nos. 13/688,970; 13/798,912 (US Publication No. 2014/0113538); and Ser. No. 14/066,354; which are hereby incorporated herein by reference.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A vent stick air freshener configured for use with a louver of an air vent, the air freshener comprising:
   a) an annular head configured to extend from the louver and having a hollow therein, an open front end and an open rear end defining an air tunnel through the annular head;
   b) a pair of vent rods extending rearwardly from the annular head and configured to extend through the louver into the air vent;
   c) a gap between the pair of vent rods configured to receive the louver;
   d) at least one body carried by at least one of the pair of vent rods;
   e) an insert at least partially received in the hollow of the annular head;
   f) a space defined between the insert and the annular head; and
   g) the at least one body or the insert or both having a desired scent material interspersed therein and diffusible out over time.

2. The device in accordance with claim 1, wherein another one of the at least one body or the insert has an odor eliminating material, different from the scent material, interspersed therein.

3. The device in accordance with claim 1, wherein both the at least one body and the insert have the desired scent material interspersed therein and diffusible out over time.

4. The device in accordance with claim 1, wherein the gap between the pair of vent rods and the hollow of the annular head are substantially collinear.

5. The device in accordance with claim 1, wherein the pair of vent rods extend from opposite sides of the annular head.

6. The device in accordance with claim 1, further comprising:
   a) at least one elongated notch formed in at least one of the pair of vent rods and receiving the at least one body therein; and
   b) the at least one body being flush with a surface of the at least one vent rod contiguous with the at least one body.

7. The device in accordance with claim 1, further comprising:
   a) at least one elongated notch formed in at least one of the pair of vent rods and receiving the at least one body therein;
   b) an aperture in the at least one elongated notch extending into the air tunnel; and
   c) the at least one body has a portion extending into the aperture and exposed to the air tunnel.

8. The device in accordance with claim 1, further comprising:
   a) at least one elongated notch formed in at least one of the pair of vent rods and receiving the at least one body therein;
   b) an aperture in the at least one elongated notch extending into the air tunnel; and
   c) the at least one body is snap fit in the at least one elongated notch, with the at least one body having a front lip extending into the aperture in the at least one elongated notch, and extending under the head.

9. The device in accordance with claim 1, wherein the head has an exterior surface with a portion laterally circumscribing the head with a concave conical shape.

10. The device in accordance with claim 1, wherein the gap between the pair of vent rods is narrower between the pair of vent rods than a diameter of the air tunnel.

11. The device in accordance with claim 1, wherein the space defined between the insert and the annular head is annular and surrounds the insert.

12. A vent stick air freshener configured for use with a louver of an air vent, the air freshener comprising:
   a) a body with a head configured to extend from the louver, and an pair of vent rods extending rearwardly from the head and configured to extend through the louver into the air vent, and with a gap between the pair of vent rods configured to receive the louver;
   b) a pair of elongated notches, each one formed in a different one of the pair of vent rods;
   c) a pair of scented bodies having a desired scent material interspersed therein and diffusible out over time, each one disposed in a different one of the pair of notches in the pair of vent rods;
   d) a cavity formed in the head of the body;
   e) an air tunnel disposed in the body and extending from the cavity in the head to the gap between the pair of vent rods;
   f) an insert at least partially received in the cavity of the head; and g) an annular gap defined between the insert and the head, and in fluid communication with the tunnel.

13. The device in accordance with claim 12, wherein the pair of scented bodies are flush with a surface of the pair of vent rods contiguous with the pair of scented bodies.

14. The device in accordance with claim 12, wherein the head has an exterior surface with a portion laterally circumscribing the head with a concave conical shape.

15. The device in accordance with claim 12, wherein the gap between the pair of vent rods is narrower between the pair of vent rods than a diameter of the air tunnel.

16. The device in accordance with claim 12, wherein each of the pair of elongated notches has an aperture therein extending into the air tunnel; and wherein the pair of scented bodies each have a portion extending into the aperture and exposed to the air tunnel.

17. The device in accordance with claim 12, wherein the pair of scent bodies is snap fit in the pair of elongated notches, with each of the pair of scent bodies having a front lip extending into an aperture in each of the pair of elongated notches, and extending under the head.

18. The device in accordance with claim 12, wherein the insert has an odor eliminating material interspersed therein, different than the scent material of the pair of scented bodies.

19. A vent stick air freshener configured for use with a louver of an air vent, the air freshener comprising:
 a) an elongated tubular body having a hollow therein and an open front end;
 b) a rear of the body being bifurcated to form a pair of vent rods configured to extend through the louver into the air vent;
 c) a gap defined between the pair of vent rods configured to receive the louver;
 d) an annular head defined in the body forward of the pair of vent rods, and configured to extend from the louver;
 e) at least one body carried by at least one of the pair of vent rods;
 f) an insert at least partially received in the hollow of the annular head;
 g) a space defined between the insert and the annular head; and
 h) the at least one body or the insert or both having a desired scent material interspersed therein and diffusible out over time.

20. The device in accordance with claim 19, wherein another one of the at least one body or the insert has an odor eliminating material, different from the scent material, interspersed therein.

21. The device in accordance with claim 19, wherein both the at least one body and the insert have the desired scent material interspersed therein and diffusible out over time.

22. The device in accordance with claim 19, further comprising:
 a) at least one elongated notch formed in at least one of the pair of vent rods and receiving the at least one body therein; and
 b) the at least one body being flush with a surface of the at least one vent rod contiguous with the at least one body.

23. The device in accordance with claim 19, further comprising:
 a) at least one elongated notch formed in at least one of the pair of vent rods and receiving the at least one body therein;
 b) an aperture in the at least one elongated notch extending into the air tunnel; and
 c) the at least one body has a portion extending into the aperture and exposed to the air tunnel.

24. The device in accordance with claim 19, further comprising:
 a) at least one elongated notch formed in at least one of the pair of vent rods and receiving the at least one body therein;
 b) an aperture in the at least one elongated notch extending into the air tunnel; and
 c) the at least one body is snap fit in the at least one elongated notch, with the at least one body having a front lip extending into the aperture in the at least one elongated notch, and extending under the head.

* * * * *